United States Patent
Sarkar et al.

(10) Patent No.: US 9,895,307 B2
(45) Date of Patent: Feb. 20, 2018

(54) PERSONAL CARE COMPOSITIONS CONTAINING IONIC SILICONE AND FILM-FORMING AGENT

(71) Applicant: Momentive Performance Materials Inc., Waterford, NY (US)

(72) Inventors: Alok Sarkar, Malda (IN); Anubhav Saxena, Bangalore (IN); Sandip Tiwari, Bangalore (IN); Benjamin Falk, Yorktown Heights, NY (US); Anne Dussaud, Tarrytown, NY (US)

(73) Assignee: Momentive Performance Materials Inc., Waterford, NY (US)

(*) Notice: Subject to any disclaimer, the term of this patent is extended or adjusted under 35 U.S.C. 154(b) by 82 days.

(21) Appl. No.: 13/734,308

(22) Filed: Jan. 4, 2013

(65) Prior Publication Data
US 2014/0017188 A1    Jan. 16, 2014

Related U.S. Application Data

(63) Continuation-in-part of application No. 13/733,482, filed on Jan. 3, 2013, and a continuation-in-part of application No. PCT/US2013/020122, filed on Jan. 3, 2013.

(60) Provisional application No. 61/582,914, filed on Jan. 4, 2012.

(51) Int. Cl.
| | |
|---|---|
| *A61K 8/899* | (2006.01) |
| *A61K 8/896* | (2006.01) |
| *A61Q 1/04* | (2006.01) |
| *A61Q 5/12* | (2006.01) |
| *A61Q 19/00* | (2006.01) |
| *A61Q 5/06* | (2006.01) |
| *A61Q 17/04* | (2006.01) |

(52) U.S. Cl.
CPC ......... *A61K 8/899* (2013.01); *A61K 8/896* (2013.01); *A61Q 1/04* (2013.01); *A61Q 5/12* (2013.01); *A61Q 19/00* (2013.01); A61K 2800/10 (2013.01); *A61Q 5/06* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 5,747,017 A * | 5/1998 | Nichols et al. | 424/61 |
| 6,071,503 A | 6/2000 | Drechsler et al. | |
| 6,124,490 A | 9/2000 | Gormley et al. | |
| 2003/0211050 A1* | 11/2003 | Majeti et al. | 424/49 |

FOREIGN PATENT DOCUMENTS

| | | | | |
|---|---|---|---|---|
| EP | 0 017 121 A1 | 10/1980 | | |
| JP | 6247835 | * 9/1994 | | A61K 7/48 |
| JP | H06 247827 | 9/1994 | | |
| JP | H06 247835 | 9/1994 | | |
| JP | H10 273414 | 10/1998 | | |
| WO | 1993/24105 A1 | 12/1993 | | |
| WO | 1993/25179 A1 | 12/1993 | | |
| WO | 1998/18431 A2 | 5/1998 | | |

OTHER PUBLICATIONS

BNSDOCID: XP002723995, Retrieved from the Internet: URL:http://ww.lubrizol.com/PersonalCare/S-G0029B-Sparkling-Gold-Hair-Styling-Gel.pdf; 2009 [retrieved on Apr. 29, 2014] the whole document.
BNSDOCID: XP002723996, Retrieved from the Internet: URL:http://ww.lubrizol.com/PersonalCare/F-0064B-Daily-UV-Defense-Moistureizer.pdf; 2009 [retrieved on Apr. 29, 2014] the whole document.
International Search Report and Written Opinion dated Mar. 21, 2014.

* cited by examiner

*Primary Examiner* — Brian Gulledge
(74) *Attorney, Agent, or Firm* — Joseph S. Ostroff

(57) ABSTRACT

A personal care composition includes at least one end-functionalized ionic silicone and at least one film-forming agent.

20 Claims, No Drawings

PERSONAL CARE COMPOSITIONS CONTAINING IONIC SILICONE AND FILM-FORMING AGENT

CROSS REFERENCE TO RELATED APPLICATIONS

This application is a continuation-in-part of U.S. patent application Ser. No. 13/733,482, filed Jan. 3, 2013, claiming the benefit of provisional U.S. patent application Ser. No. 61/582,914, filed Jan. 4, 2012, the entire contents of these benefit applications being incorporated by reference herein.

BACKGROUND OF THE INVENTION

This invention relates to the personal care compositions containing one or more ionic silicone components and at least one film-forming agent.

Personal care products formulated with ionic silicones are known as are personal care product formulated with chemically crosslinked polymer film formers. However, personal care products containing both an ionic silicone component and a film-forming agent are not believed to have heretofore been described.

SUMMARY OF THE INVENTION

In accordance with the present invention, a personal care composition is provided which comprises:

(a) at least one end-functionalized ionic silicone of the formula:

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{1/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ in which:
$R^1$, $R^2$, $R^3$, $R^5$, $R^6$, $R^8$, $R^9$, $R^{10}$, $R^{11}$, $R^{13}$, $R^{15}$ and $R^{16}$ each independently is an aliphatic, aromatic or fluoro monovalent hydrocarbon group having from 1 to 60 carbon atoms;

$R^4$, $R^{12}$ and $R^{17}$ each independently is a monovalent group bearing ion-pairs and having the formula $-A-I^{x-}\cdot M_n^{y+}$, or zwitterion having the formula $-R'-N^+(R'')_2-R'''-I^-$, in which A is a spacing moiety having at least one spacing atom, the spacing moiety being selected from the group consisting of divalent hydrocarbon group and hydrocarbonoxy group, I is an ionic group, R' is a divalent hydrocarbon group having from 1 to 20 carbon atoms, R'' is a monovalent hydrocarbon group having from 1 to 20 carbon atoms, R''' is a divalent hydrocarbon group having from 2 to 20 carbon atoms, and each M independently is hydrogen or a cation independently selected from alkali metals, alkali earth metals, transition metals, quaternary ammonium groups and phosphonium groups;

$R^7$, $R^{14}$ and $R^{18}$ each independently is $-CH_2CH(R^{19})(C_nH_{2n})-O-(C_2H_4O)_o-(C_3H_6O)_p-(C_4H_8O)_q-R^{19}$ in which $R^{19}$ is hydrogen or an $R^1$ group as defined above;

superscripts x and y are positive integers subject to the limitation that x=ny;

each subscript n independently has a value of from 0 to 6 and subscripts o, p and q each independently has a value of from 0 to 1000, subject to the limitation that o+p+q≥1; and, subscripts a, c, d, e, f, g, h, i and j each independently is zero or a positive integer subject to the limitations that 2≤a+b+c+d+e+f+g+h+i+j≤4500 and b≥2; and, (b) from 0.1 to 99 parts by weight of at least one film-forming agent.

The end-functionalized ionic silicone component of the personal care composition of the present invention forms aggregates of the ionic groups to ion rich domains of specific dimensions which act as the ionic filler to the composition. These ionic aggregates act as crosslinks and increase the modulus of the composition. Unlike chemically crosslinked polymer film formers where once the crosslinks are broken due to some external applied force (e.g., heat or shear) causing the system to permanently lose its integrity, ionic crosslinks when subjected to such an external force cause the ionic clusters to disaggregate and reform as aggregates when the applied force is removed. However, due to the relatively lower bond strength of the ionic bond, personal care compositions formulated with ionic silicones alone may not be sufficient to provide the same magnitude of benefits compared to similar personal care compositions formulated with known and conventional chemically crosslinked polymer film-forming agents.

DETAILED DESCRIPTION OF PREFERRED EMBODIMENTS

In the specification and claims herein, the following terms and expressions are to be understood as indicated.

As used in the specification and including the appended claims, the singular forms "a," "an," and "the" include the plural, and reference to a particular numerical value includes at least that particular value unless the context clearly indicates otherwise.

Other than in the working examples or where otherwise indicated, numerical values and ranges of numerical values herein whether or not modified by such terms as "about" and "approximately" are to be understood to include the indicated value(s) and value(s) approximate thereto. When such a range is expressed, another embodiment includes from the one particular value and/or to the other particular value. Similarly, when values are expressed as approximations, e.g., by use of the modifier "about," it will be understood that the particular value forms another embodiment.

It will also be understood that any numerical range recited herein is intended to include all sub-ranges within that range.

All methods described herein may be performed in any suitable order unless otherwise indicated or clearly contrary to context. The use herein of any and all examples or exemplification language (e.g., "such as"), is intended merely to better illustrate the invention and does not pose a limitation on the scope of the invention unless otherwise claimed. No language in the specification should be construed as indicating any non-claimed element as essential to the practice of the invention.

As used herein, the terms "comprising," "including," "containing," "characterized by" and grammatical equivalents thereof are inclusive or open-ended terms that do not exclude additional, unrecited elements or method steps and are also to be understood as including the more restrictive terms "consisting of" and "consisting essentially of."

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

End-functionalized ionic silicones (I) of the present invention form aggregates of the ionic groups to ion-rich domains, having dimensions, e.g., from 40 to 200 nm, which serve as ionic filler in the composition. These ionic aggregates act as crosslinks and increase the modulus of the material. In addition to acting as crosslinks, the aggregates also behave as reinforcing filler particles and as such may further increase the modulus of the personal care composition containing them. Moreover, due to the reversible nature of the ionic interactions, when heated to a certain level (e.g., ca. 180° C.) the ionic aggregates disaggregate somewhat to form relatively more thermodynamically stable ionic aggregates upon cooling. As a consequence of this phenomenon, the viscosity of these materials keeps increasing during repeated heating/cooling cycles. In addition, the ionic aggregates can be dissolved in a polar solvent such as water then reformed with the removal of the solvent. The presence of ionic groups also helps to make silicones (I) exceptionally compatible with hydrophilic and lipophilic components commonly utilized in such personal care compositions as moisturizers, sunscreens, and the like.

The foregoing unique physicochemical properties of end-functionalized ionic silicones (I) is believed to play an important role in providing such highly desirable product performance characteristics as high transfer resistance and high gloss in lip color formulations, controlled release of actives and substantives in sunscreen agents and other personal care compositions, and the like.

In end-functionalized ionic silicone (I) herein, each $R^1$, $R^2$, $R^3$, $R^5$, $R^6$, $R^8$, $R^9$, $R^{10}$, $R^{11}$, $R^{13}$, $R^{15}$ and $R^{16}$ group is preferably methyl, ethyl, n-propyl, iso-propyl, n-butyl, isobutyl, tert-butyl, n-pentyl, iso-pentyl, neopentyl, tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Representative aromatic groups include phenyl, naphthyl; o-, m- and p-tolyl, xylyl, ethylphenyl and benzyl.

In groups $R^4$, $R^{12}$ and $R^{17}$, divalent hydrocarbon spacing group A of ion-pair $-A-I^{x-}-M_n^{y+}$ can be, e.g., an alkylene group such as $-(CHR^{20})_m-$ wherein $R^{20}$ is hydrogen or an $R^1$ group as defined above and subscript m is a positive integer ranging from 1 to 100 and preferably from 1 to 20; or an arylene group such as $-(CHR^{21})_kC_6H_4(CH_2)_r-$ $-CH^2CH(R')(CH_2)_kC_6H_4-$ or $-CH_2CH(R^{22})(CH_2)_r-$ $C_6H_3R^{23}$ wherein R' is hydrogen or an R' group as defined above, $R^{21}$ is hydrogen or an $R^1$ group as defined above, $R^{22}$ is hydrogen or an $R^1$ group as defined above, $R^{23}$ is a monovalent radical of from 1 to 20 carbon atoms and subscripts k and r are zero or positive integers subject to the limitation $0 \leq k+r \leq 100$.

Divalent hydrocarbon spacing group A can also be, e.g., a divalent hydrocarbonoxy group such as $-(CHR^{24})_s-$ $(O-CHR^{24}CH_2)_{s'}-O-(CH_2)_t$ wherein $R^{24}$ is hydrogen or an $R^1$ group as defined above, s has a value of from 0 to 50, s' has a value of from 1 to 50 and t has a value of from 0 to 50 subject to the limitation $1 \leq s+s'+t \leq 100$.

$I^-$ in the ion-pair-bearing group and in the zwitterion is preferably an ionic group such as sulfonate $-SO_3^-$, sulfate $-OSO_3^-$, and the like.

Examples of cation $M^+$ include Li, Na, K, Cs, Mg, Ca, Ba, Zn, Cu, Fe, Ni, Ga, Al, Mn, Cr, Ag, Au, Pt, Pd, Ru and Rh.

In the zwitterion, R' is a divalent hydrocarbon radical having from 1 to 20 carbon atoms, e.g., $-(CH_2)_s-$; R" is a monovalent hydrocarbon radical having from 1 to 20 carbon atoms, e.g., $-CH_2CH_3$; and, R''' is a divalent hydrocarbon radical having from 2 to 20 carbon atoms, e.g., $-(CH_2)_4-$.

In end-functionalized ionic silicone (I), $R^7$, $R^{14}$ and $R^{18}$ each independently is $CH_2CH(R^{19})(C_nH_{2n})-O-(C_2H_4O)_o$ $-(C_3H_6O)_p-(C_4H_8O)_q-R^{19}$ wherein $R^{19}$ is hydrogen or an $R^1$ group as defined above, each subscript n independently has a value of from 0 to 6 and subscripts o, p and q each independently has a value subject to the limitation that $o+p+q \geq 1$.

In end-functionalized ionic silicone (I), subscripts a, c, d, e, f, g, h, i and j each independently is zero or a positive number subject to the limitations that $2 \geq a+b+c+d+e+f+g+h+i+j \geq 4500$, $b \geq 2$. In one embodiment, subscript b is 2; subscripts a, c, e, f, g, h, i, j, k, l and m are 0; subscript d is from 5 to 1000, more preferably from 10 to 500, and most preferably from 10 to 200; $R^5$, $R^6$, $R^{10}$ and $R^{11}$ are methyl or ethyl; $R^{10}$ is $-CH_2CH(H$ or $CH_3)-A-SO_3M$; A is a divalent benzyl radical; and, M is Li, Na, K, silver, or a quaternary ammonium group, ammonium salt or phosphonium group.

Examples of ionic silicone (I) include sodium sulfonate-capped polydimethylsiloxane, silver sulfonate-capped polydimethylsiloxane, magnesium sulfonate-capped polydimethylsiloxane, calcium sulfonate-capped polydimethylsiloxane, zinc sulfonate-capped polydimethylsiloxane and triethanolammonium sulfonate-capped polydimethylsilane.

The film-forming agents according to the present invention include, but are not limited to, organosiloxane resins, hydrocarbon polymers, hydrocarbon polymer containing heteroatoms, fluorine atom containing hydrocarbon polymers, and clays.

Useful organosiloxane film-forming agents may comprise combinations of $R_3SiO_{1/2}$, $R_2SiO$, $RSiO_{3/2}$, and $SiO_2$ units in ratios to each other that satisfy the relationship $R_nSiO_{(4-n)/2}$ where n is a value between 0 and 1.50 and R is independently selected from methyl, trifluoromethyl, phenylenemethyl and phenyl groups.

Useful hydrocarbon polymer film-forming agents in accordance with the present invention may be selected from, but are not limited to, polybutene, polyisobutene, polycyclopentadiene, petroleum jelly and mineral oil.

The hydrocarbon polymers containing at least one heteroatom that are useful as film-forming agents in accordance with the present invention may be selected from, but are not limited, to polyvinylpyrrolidone (PVP)/eicosene Copolymer, PVP/hexadecene Copolymer, acrylate copolymer and polyvinyl alcohol.

Useful film-forming clays in accordance with the present invention may include various modified and unmodified clays including cloisite 30B, momtmorillite (NaMMT), LDH and bentonite.

Personal care compositions in accordance with the present invention include, but are not limited to deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations comprising at least one of the foregoing personal care applications.

The personal care composition of the present invention may optionally contain up to 90 parts by weight of one or more pigments. Pigments suitable for use herein are all inorganic and organic colors/pigments. These are usually aluminum, barium or calcium salts or lakes. A lake is a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Other colors and pigments can also be included in the compositions, such as pearls, titanium oxides, Red 6, Red 21, Blue 1, Orange 5, and Green 5 dyes, chalk, talc, iron oxides and titanated micas.

The personal care composition of the present invention may optionally contain up to 99 parts by weight of one or more known or conventional cosmetically-acceptable organic film former. Examples of useful film-forming agents include natural waxes, polymers such as polyethylene polymers, copolymers of PVP, ethylene vinyl acetate, dimethicone gum, resins such as shellac, polyterpenes, and the like.

The personal care composition of the present invention may optionally include up to 50 parts by weight of blocking and/or absorbing sunscreen agents. Blocking sunscreen agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreen agents, which are usually organic species, include, but are not limited to, UV-A absorbers, which generally absorb radiation in the 320 to 400 nm region of the ultraviolet spectrum, e.g., anthranilates, benzophenones and dibenzoyl methanes; and, UV-B absorbers, which generally absorb radiation in the 280 to 320 nm region of the ultraviolet spectrum, e.g., p-aminobenzoic acid derivatives, camphor derivatives, cinnamates and salicylates.

Specific examples of organic sunscreen agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexylp-methoxycinnamate, 2-ethyihexyl salicylate, glyceryl aminobenzoate, homomenthyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethyihexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo) benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4,6-tris-(2'-ethylhexyl-1'-oxycarbonyl)-anilinol 1,3,5-triazine, 2-(p-(tert-butylamido)anilinol-4,6-bis-(p-(2'-ethylhexyl 1'-oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden) methylbenzyl acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (drometrizole trisiloxane), solubilized 2,2'-methylene-bis-1,6-(2H-benzotriazol-2-yl)-4-(1,1,3,3-tetramethylbutyl) phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreen agents.

In one embodiment, it has been found that a combination of at least three sunscreen agents is especially effective. In another embodiment, it has been found that a combination of four sunscreen agents is particularly effective, especially where chemical sunscreen agents are used.

The personal care composition herein is specifically formulated for use as a color cosmetic, sunscreen, hair conditioner and a moisturizer. Suitable forms and formulations for such application are known to those of ordinary skill in the art. For example, when formulated for use as a sunscreen, the composition may be in the form of a lamellar emulsion, a microemulsion, or a nanoemulsion. In addition, the emulsion may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets.

In one embodiment, the sunscreen application is an emulsion having a continuous aqueous phase, and may be in the form of a stick, a lotion, a gel, a spray, and the like. Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C) available from Momentive Performance Materials Inc., cyclopentasiloxane and dimethicone copolyol, are also available from Momentive Performance Materials, Inc.

Plasticizers may also be added to the sunscreen formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

The composition of the present invention is preferentially incorporated into a carrier, specifically a volatile carrier which quickly volatilizes after application. The volatile carriers of the present invention are selected from the group consisting of volatile hydrocarbons, volatile silicones and mixtures thereof. Hydrocarbon oils useful in the present invention include those having boiling points in the range of 60-260° C., more preferably hydrocarbon oils having from about $C_8$ to about $C_{20}$ chain lengths, most preferably $C_8$ to $C_{20}$ isoparaffins. Most preferred are selected from the group consisting of isododecane, isohexadecane, isoeocosane, 2,2,4-trimethylpentane, 2,3-dimethylhexane and mixtures thereof. Preferred volatile silicone fluids include cyclomethicones having 3, 4 and 5 membered ring structures corresponding to the formula $(R_2SiO)_x$, where x is from about 3 to about 6 or linear methicones corresponding to the formula $(R_3SiO(R_2SiO)_xSiR_3$ where x is from about 0 to about 6.

A thickening polymer may be useful in the present invention. The expression "thickening polymer" shall be understood for the purposes of the present invention to mean a polymer having, in solution or in dispersion containing 1% by weight of active material in water or in ethanol at 25° C., a viscosity greater than 0.2 poise at a shear rate of 1 s-I. The viscosity can be measured with a HAAKE RS600 viscometer from THERMO ELECTRON. This viscometer is a controlled-stress viscometer with cone-plate geometry (for example, having a diameter of 60 mm and an angle of 1°). Examples of thickeners include; associative thickeners; crosslinked acrylic acid homopolymers; crosslinked copolymers of (meth)acrylic acid and of ($C_1$-$C_6$)alkyl acrylate; nonionic homopolymers and copolymers containing ethylenically unsaturated monomers of ester and/or amide type; ammonium acrylate homopolymers or copolymers of ammonium acrylate and of acrylamide; (meth)acrylamido ($C_1$-$C_4$)alkylsulphonic acid homopolymers and copolymers; crosslinked methacryloyl($C_1$-$C_4$)alkyltri($C_1$-$C_4$)alkylammonium homopolymers and copolymers. Particulate thickeners may also be used. Also, naturally derived polymers and polymers produced by fermentations may be used such as polysaccharide gums, xanthan gum, pullulan gum, sclerotium gum, carrageenan gum, locust bean gum, alginate, gellan gum, cellulose, carboxymethylcellulose, hydroxyethylcellulose, pectins, starch, chitosan, gelatin and their combination.

Particulates may also be used in combination with the personal care composition of the present invention. Particulates may be organic or inorganic particles. Examples of inorganic particles include microparticles composed of titanium oxide, titanated mica, zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, lepidolite, biotite, lithia mica, silicic acid, silicon dioxide, fumed silica, hydrous silicon dioxide, aluminum silicate, magnesium silicate, aluminum magnesium silicate, calcium silicate, barium silicate, strontium silicate, metal tungstenate salts, hydroxyapatite, vermiculite, higilite, bentonite, montmorillonite, hectorite, zeolite, ceramics, dicalcium phosphate, alumina, aluminum hydroxide, boron nitride, boron nitride or glass, Example of organic particles include powders composed of a polyamide, polyacrylic acid/acrylic acid ester, polyester, polyethylene, polypropylene, polystyrene, styrene/acrylic acid copolymer, divinylbenzene/styrene copolymer, polyurethane, vinyl resin, urea resin, melamine resin, benzoguanamine, polymethylbenzoguanamine, tetrafluoroethylene, polymethylmethacrylate (such as poly(methyl methacrylate)), cellulose, silk, nylon, phenol resin, epoxy resin or polycarbonate.

Useful additives include pH adjusters/buffering agents and chelating agents such as ammonium hydroxide, sodium hydroxide, potassium hydroxide, $C_{12}$-$C_{15}$ alkyl benzoate, citric acid, glycolic acid, lactic acid, sodium citrate, triethanolamine, trolamine, disodium EDTA, edetate disodium, pentasodium pentetate, tetrasodium EDTA, trisodium EDTA.

Fragrance ingredients may be incorporated in the personal care composition of the present invention, e.g., diacetyl, isoamyl acetate, benzaldehyde, cinnamic aldehyde, ethyl propionate, methyl anthranilate, limonene, ethyl decadienoate, allyl hexanoate, ethyl maltol, ethyl vanillin, methyl salicylate, clary extract, eucalyphis globulus oil, grapefruit oil, labdanum oil, masking fragrance, matricaria oil, nopyl acetate, phenoxyethanol, rosewood oil, ylang ylang oil, and perfume oils. There may also be mentioned as perfume oils mixtures of natural and/or synthetic aromatic substances. Natural aromatic substances include, e.g., extracts from blossom (lilies, lavender, roses, jasmine, neroli, ylang-ylang), from stems and leaves (geranium, patchouli, petit-grain), from fruit (aniseed, coriander, carraway, juniper), from fruit peel (bergamot, lemons, oranges), from roots (mace, *angelica*, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances include, e.g., products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate.

Ethers include, e.g., benzyl ethyl ether; the aldehydes include, e.g., linear alkanals having from 8 to 18 hydrocarbon atoms, citral, citronellal, citronellyl oxyacetaldehyde, cyclamen aldehyde, hydroxycitronellal, lilial and bourgeonal; ketones include, e.g., ionones, isomethylionone and methyl cedryl ketone; alcohols include, e.g., anethol, citronellol, eugenol, isoeugenol, geraniol, linalool, phenyl ethyl alcohol and terpinol; and, hydrocarbons include, e.g., terpenes and balsams.

It is preferable to use mixtures of these and other aromatic substances in combinations that produce an especially attractive scent. Ethereal oils of relatively low volatility, which are chiefly used as aroma components, are also suitable as perfume oils, e.g., sage oil, chamomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α,α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, α-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Flavor ingredients may be used in the personal care composition of the present invention such as stearyl glycyrrhetinate, menthol, cinnamyl alcohol, acetic acid, ascorbic acid, citric acid, fumaric acid, lactic acid malic acid, phosphoric acid, tartaric acid, fruit and plant extracts.

Skin protectants and humectants may be used in the personal care composition of the present invention such as dimethicone, petrolatum, glycerin, ammonium lactate, lanolin, methyl gluceth-20, PEG-20, sorbitol, 1,2,6 hexanetriol, butylene glycol, dipropylene glycol, glycerin, hexylene glycol, panthenol, phytantriol, panthenol, propylene glycol, sodium PCA, sorbitol, triethylene glycol, polyglyceryl sorbitol, glucose, fructose, polydextrose, potassium pca, urea, hydrogenated honey, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, and the like.

Hair conditioning agents may be used herein, e.g., hydrocarbons, silicone fluids and cationic materials. Suitable hydrocarbons can be either straight or branched chain and can contain from about 10 to about 16, and preferably from about 12 to about 16, carbon atoms. Examples of suitable hydrocarbons include, e.g., decane, dodecane, tetradecane, tridecane, and mixtures thereof. Examples of suitable silicone fluid conditioning agents include, e.g., linear and cyclic polydimethylsiloxanes, phenyl and alkyl phenyl silicones and silicone copolyols. Cationic conditioning materials agents useful herein include, e.g., quaternary ammonium salts and the salts of fatty amines.

Nail conditioning agents may be incorporated in the present invention, e.g., adipic acid, fumaric acid, tricyclodecane dimethanol copolymer, AMP-isostearoyl hydrolyzed silk, *angelica furcijuga* flower/leaf/stem extract, r-*bacillus licheniformis* keratinase, *bifida/panax* ginseng root cell culture extract ferment filtrate, bis-aminopropyl dimethicone/IPDI copolymer, bis-dicaprolactone ethoxyacrylate IPDI, bis-hEMA IPDI, *boswellia carterii* gum extract, *boswellia serrata* gum extract, calcium hydrolyzed collagen, capryloyl methionine/silk amino acids methyl esters, capryloyl serine/silk amino acid methyl esters, *caulerpa eacemosa* extract, citrus *aurantium amara* (bitter orange) fruit juice extract, *commelina communis* flower/leaf/stem extract, *commiphora myrrha* resin extract, dechloro dihydroxy difluoro ethylcloprostenolamide, deoxyglutamyl fructose, dicaprolactone ethoxyacrylate hema ipdi, dicapryl succinate, dimethyl urea, dipentaerythrityl hexaacrylate, dipentaerythrityl pentaacrylate, *echinacea angustifolia* root extract, *fragaria ananassa* (strawberry) seed oil, fumaric acid/phthalic anhydride/tricyclodecanedimethanol copolymer, ginkgo biloba nut extract, glycidoxypropyl trimethoxysilane, honey powder, *hydnocarpus pentandrus* kernel oil, hydrogenated acetophenone/oxymethylene copolymer, hydrolyzed collagen, hydrolyzed keratin, hydrolyzed vinylacetate/vinyl acetoacetate copolymer, isatis tinctoria root extract, *kigelia africana* bark extract, leucanthemum vulgare seed extract, leuconostoc/*aloe barbadensis* leaf/*sorbus aucuparia* fruit ferment filtrate, *lobelia inflata* extract, *lupinus texensis* seed extract, *lycium barbarum* fruit extract, *mentha aquatica* extract, methacryloylethyl phosphate, methylene glycol, 2-methylpropanal, *momordica charantia* extract, *narcissus pseudonarcissus* (daffodil) root extract, *opuntia tuna* leaf extract, *opuntia vulgaris* fruit extract, palmitoyl oligopeptide-70, palmitoyl serine/silk amino acids methyl esters, *phaseolus vulgaris* (kidney bean) extract, phlox drummondii seed extract, polyacrylate-12, polyacrylate-30, polyester-18, *rosa* (american beauty) extract, *rosa borboniana* extract, *rosa roxburghii* seed oil, *rudbeckia hirta* seed extract, silver carp extract, sodium calcium zinc phosphate, *sorbus aucuparia* seed oil, r-spider polypeptide-1, r-spider polypeptide-2, undecenoyl serine/silk amino acid methyl esters, *vaccinium myrtillus* leaf extract, vinyl alcohol/vinylformamide copolymer, *viscum album* (mistletoe) extract, and the like.

Cationic polymers can be used in the personal care composition of the present invention, e.g., cationic guar gum derivatives such as guar hydroxypropyltrimonium chloride and hydroxypropyl guar hydroxypropyltrimonium chloride, available as the Jaguar® series from Rhone-Poulenc.

Ultraviolet light absorbers (UV absorbers) may be useful utilized in the personal care composition herein to protect the composition from chemical or physical deterioration induced by ultraviolet light. UV absorbers, like the sunscreen agents, supra, have the ability to convert incident ultraviolet radiation into less damaging infrared radiation (heat). Suitable UV absorbers include e.g., acetaminosalol, allantoin PABA, benzalphthalide, benzophenones such a benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, and phenone-12, benzotriazolyl dodecyl p-cresol, 3-benzylidene camphor, benzylidenecamphor hydrolyzed collagen sulfonamide, benzylidene camphor sulfonic acid, benzyl salicylate, bis-ethylhexyloxyphenol methoxyphenyl triazine, bornelone, bumetrizole, butyl methoxydibenzoylmethane, butyl PABA, *Callophyllum inophyllum* Seed Oil, *camellia sinensis* leaf extract, carotenoids, ceria/silica, ceria/silica talc, cinoxate, dea-methoxycinnamate, dibenzoxazoyl naphthalene, di-t-butyl hydroxybenzylidene camphor, diethylhexyl butamido triazone, diethylhexyl 2,6-naphthalate, digalloyl trioleate, diisopropyl methyl cinnamate, 1-(3,4-dimethoxyphenyl)-4,4-dimethyl-1,3-pentanediene, dimethyl PABA ethyl cetearyldimonium tosylate, dimorpholinopyridazinone, diphenyl carbomethoxy acetoxy naphthopyran, disodium bisethylphenyl triaminotriazine stilbenedisulfonate, disodium distyrylbiphenyl disulfonate, disodium phenyl dibenzimidazole tetrasulfonate, drometrizole, drometrizole trisiloxane, esculin, ethyl dihydroxypropyl PABA, ethyl diisopropylcinnamate, ethylhexyl dimethoxybenzylidene dioxoimidazolidine propionate, ethylhexyl dimethyl PABA, ethylhexyl ferulate, ethylhexyl methoxycinnamate, ethylhexyl salicylate, ethylhexyl triazone, ethyl methoxycinnamate, ethyl PABA, ethyl urocanate, etocrylene, ferulic acid, 4-(2-beta-glucopyranosiloxy)propoxy-2-hydroxybenzophenone, glyceryl ethylhexanoate dimethoxycinnamate, glyceryl PABA, glycol salicylate, hexanediol salicylate, homosalate, hydrolyzed lupine protein, isoamyl p-methoxycinnamate, isopentyl trimethoxycinnamate trisiloxane, isopropylbenzyl salicylate, isopropyl dibenzoylmethane, isopropyl methoxycinnamate, menthyl anthranilate, menthyl salicylate, 4-methylbenzylidene camphor, methylene bis-benzotriazolyl tetramethylbutylphenol, octocrylene, octrizole, PABA, PEG-25 PABA, pentyl dimethyl PABA, phenylbenzimidazole sulfonic acid, *pinus pinaster* bark extract, polyacrylamidomethyl benzylidene camphor, polysilicone-15, potassium methoxycinnamate, potassium phenylbenzimidazole sulfonate, Red petrolatum, sodium benzotriazolyl butylphenol sulfonate, sodium isoferulate, sodium phenylbenzimidazole sulfonate, sodium urocanate, *Spirulina platensis* powder, tea-phenylbenzimidazole sulfonate, TEA-salicylate, terephthalylidene dicamphor sulfonic acid, tetrabutyl phenyl hydroxybenzoate, titanium dioxide, tocotrienols, triPABA panthenol, urocanic acid, vinyl acetate/crotonates/methacryloxybenzophenone-1 copolymer and Vitis vinifera (grape) seed extract, and polymeric beads or hollow spheres as SPF enhancers. The combination of the UV-absorbers such as those described above with SPF enhancers such as styrene/acrylate copolymers silica beads, spheroidal magnesium silicate, spherical polyamide powder such as n-lactam polymer (Orgasol® range, elf atochem) crosslinked polymethylmethacrylates (pmma; micopearl m305 seppic), may enhance the UV protection. Holosphere additives (Sunspheres® ISP, Silica Shells Kobo.) deflect radiation and the effective path length of the photon is therefore increased. (EP0893119). Some beads, provide a soft feel during spreading. Moreover, the optical activity of such beads, e.g., Micropearl M305, can modulate skin shine by eliminating reflection phenomena and indirectly may scatter UV light.

The personal care composition of the present invention may also contain one or more known and conventional plasticizers in order to improve the flexibility and cosmetic properties of the resulting formulation. Plasticizers are frequently used to avoid brittleness and cracking of film formers and include, e.g., lecithin, polysorbates, dimethicone copolyol, glycols, citrate esters, glycerin, and dimethicone. One skilled in the art may routinely vary the amount of plasticizer(s) depending on the formulation of a particular personal care composition and the properties desired.

The personal care composition of the present invention is advantageously formulated with a carrier, specifically, a volatile carrier which quickly volatilizes after application of the composition. Useful volatile carriers may be selected from the group consisting of volatile hydrocarbons, volatile silicones and mixtures thereof.

Hydrocarbon oils useful in the present invention include those having boiling points in the range of 60-260° C., more preferably hydrocarbon oils having from about $C_8$ to about $C_{20}$ chain lengths, most preferably $C_8$ to $C_{20}$ isoparaffins. Most preferred are isododecane, isohexadecane, isoeocosane, 2,2,4-trimethylpentane, 2,3-dimethylhexane and mixtures thereof.

EXAMPLES

Examples 1-12 below illustrate the preparation of end-functionalized ionic silicones (I) for subsequent combination with film-forming agents in accordance with the present invention.

Example 1

Preparation of Sulfonic Acid-functionalized Tetramethyldisiloxane.

A three necked 500 mL flask was charged with 18.16 g (154.0 mmol) alpha-methylstyrene and $27.2 \times 10^{-5}$ g platinum catalyst. The temperature of the resulting mixture was brought to 115° C., then 9.40 g (70.0 mmol) 1,1,3,3 tetramethyldisiloxane was added drop wise and continued to stir until completion of the hydrosilylation reaction. The complete hydrosilylation was indicated by the disappearance of silicone hydride peak in the $^1$H NMR. The resulting mixture was vacuum stripped to remove unreacted alpha-methylstyrene by placing on an oil bath at 150° C. for 2 h which gave 23.2 g aralkylene substituted disiloxane. (Yield: 90%).

To this aralkylene substituted disiloxane (23.2 g, 62.4 mmol), 29.6 g (252.8 mmol) of chlorosulfonic acid was added drop wise through a period of 30 minutes while the mixture being stirred at room temperature. The resulting mixture was continued to stir for additional 30 minutes. The completion of the reaction was determined by $^1$H NMR where total sulfonation of the aromatic ring was indicated by the disappearance of para-substituted aromatic proton peak. The vacuum stripping of the reaction mixture at low pressure afforded 33.0 g of the sulfonated disiloxane as brown viscous oil.

Example 2

Preparation of Sulfonic Acid-Functionalized Tetramethyltetracyclosiloxane.

A three necked 500 mL flask was charged with 70.08 g (60.0 mmol) alpha-methylstyrene and $10.0 \times 10^{-4}$ g platinum catalyst. The temperature of the resulting mixture was brought to 115° C., then 30.0 g (120.5 mmol) 1,3,5,7-tetramethylcyclotetrasiloxane was added drop wise and continued to stir. The progress of the reaction mixture was monitored by $^1$H NMR. After 12 h of the reaction, complete conversion of silicone hydride was indicated by the NMR. Then, the reaction mixture was vacuum stripped at 150° C. for 2 h to remove unreacted alpha-methylstyrene which gave 80.5 g aralkylene substituted cyclotetrasiloxane. (Yield: 95%).

To 14.24 g (20.0 mmol) of the above aralkylene substituted cyclotetrasiloxane, 18.64 g (160.0 mmol) chlorosulfonic acid dissolved in 4.0 mL dichloromethane was added drop wise through a period of 30 minutes while the mixture being stirred at room temperature. The resulting mixture was continued to stir for an additional 30 minutes. The completion of the reaction was indicated by $^1$H NMR where complete sulfonation of the aromatic ring was indicated by the disappearance of para-substituted aromatic proton peak. The vacuum stripping of the reaction mixture at low pressure afforded 20.6 g of the sulfonic acid functional cyclotetrasiloxane as brown viscous gum.

Example 3

Preparation of Sodium Sulfonate-Capped Polydimethylsiloxane.

A three necked 250 mL flask was charged with 1.1 g (2.0 mmol) sulfonated disiloxane (from example 1), 59.3 (200.0 mmol) octamethyltetracyclosiloxane. After reaching an equilibrium of ~87 wt % of the linear siloxanes, the reaction mixture was neutralized using 0.7 g (8.0 mmol) moistened sodium bicarbonate at 70° C. The vacuum stripping of the reaction mixture at low pressure afforded 49.0 g of the product as viscous gum. The NMR analysis of the product indicated that the polymer was a sulfonated-capped polydimethylsiloxane. The polymer had a viscosity of 53 Pas at a shear rate of 10 rad/s when measured by a HAAKE Rheometer at 20° C.

Similarly, Calcium, Magnesium, Zinc, silver and cobalt salt of sulfonate-capped polydimethylsiloxanes (PDMS) have been synthesized via neutralizing the sulfonic acid capped PDMS with the respective oxide.

Example 4

Preparation of Sodium Sulfonate-Capped Polydimethylsiloxane.

A three necked 250 mL flask was charged with 2.12 g (4.0 mmol) sulfonated disiloxane (from example 1), 59.3 g (200.0 mmol) octamethyltetracyclosiloxane. The reaction mixture was placed into an oil bath and continued to stir room temperature. After reaching an equilibrium of ~87 wt % of the linear siloxanes, the reaction mixture was neutralized using 1.4 g (16.0 mmol) moistened sodium bicarbonate at 70° C. The vacuum stripping of the reaction mixture at low pressure afforded 53.0 g of the product as viscous gum. The NMR analysis of the product indicated that the polymer was a sulfonated-capped polydimethylsiloxane. The polymer had a viscosity of 100 Pas at a shear rate of 10 rad/s when measured by a HAAKE Rheometer at 20° C.

Example 5

Preparation of Sodium Sulfonate-Capped Polydimethylsiloxane.

A three necked 500 mL flask was charged with 10.6 g (20.0 mmol) sulfonated disiloxane (from example 1), 118.0 g (400.0 mmol) octamethyltetracyclosiloxane. The reaction mixture was placed into an oil bath and continued to stir at room temperature. After reaching an equilibrium of ~87 wt % of the linear siloxanes, the reaction mixture was neutralized using 6.7 g (80.0 mmol) moistened sodium bicarbonate at 70° C. The vacuum stripping of the reaction mixture at low pressure afforded 112.0 g of the product as viscous gum. The NMR analysis of the product indicated that the polymer was a sulfonated-capped polydimethylsiloxane. The polymer had a viscosity of 1230 Pas at a shear rate of 10 rad/s when measured by a HAAKE Rheometer at 20° C.

Example 6

Preparation of Pendant Sulfonate-Functional Polyorganosiloxane

To the sulfonic acid functional cyclotetrasiloxane 5.7 g (8.0 mmol) obtained in example 2, 474.7 g (1600.0 mmol) octamethyltetracyclosiloxane and 2.96 g (16.0 mmol) 1,1,3,3-tetramethyl-1,3-divinyldisiloxane were added and continued to stir at room temperature. After reaching equilibrium of ~87 wt % of the linear siloxanes, the reaction mixture was neutralized using 10.0 g (128.0 mmol) moistened sodium bicarbonate at 70° C. The vacuum stripping of the reaction mixture at low pressure afforded 411.0 g of the product as Milky oil. The NMR analysis of the product indicated that the polymer was a pendant polydimethylsiloxane. The polymer had a viscosity of 5.0 Pas at a shear rate of 10 rad/s when measured by a HAAKE Rheometer at 20° C.

To the sulfonic acid functional cyclotetrasiloxane 5.7 g (8.0 mmol) obtained in example 2, 474.7 g (1600.0 mmol) octamethyltetracyclosiloxane and 14.8 g (80.0 mmol) 1,1,3,3-tetramethyl-1,3-divinyldisiloxane were added and continued to stir at room temperature. After reaching equilibrium of ~87 wt % of the linear siloxanes, the reaction mixture was neutralized using 10.0 g (128.0 mmol) moistened sodium bicarbonate at 70° C. The vacuum stripping of the reaction mixture at low pressure afforded 427.0 g of the product as viscous gum. The NMR analysis of the product indicated that the polymer was a pendant polydimethylsiloxane.

Example 7

Preparation of Pendant Sulfonate-Functional Polyorganosiloxane.

To the sulfonic acid functional cyclotetrasiloxane 5.7 g (8.0 mmol) obtained in example 2, 474.7 g (1600.0 mmol) octamethyltetracyclosiloxane and 14.8 g (80.0 mmol) 1,1,3,3-tetramethyl-1,3-divinyldisiloxane were added and continued to stir at room temperature. After reaching equilibrium of ~87 wt % of the linear siloxanes, the reaction mixture was neutralized using 10.0 g (128.0 mmol) moistened sodium bicarbonate at 70° C. The vacuum stripping of the reaction mixture at low pressure afforded 427.0 g of the product as viscous gum. The NMR analysis of the product indicated that the polymer was a pendant polydimethylsiloxane.

Example 8

Preparation of Sodium Carboxylate-Functional Polydimethylsiloxane.

A 1000 ml three necked round bottom flask, equipped with condenser, was charged with 184.28 g (1M) Undecenoic acid and 300 ml toluene. The solution was heated to 70° C. and added 80.7 g (0.5M) Hexamethyldisilazane over the period of 2 h. The solution was stirrer at 70-80° C. for 4 h. The solution was stripped off the solvent and the reaction mass was distilled under vacuum at 1-5 Hg pressure and 150-160° C. to give Undecenoic acid trimethylsilylester (A).

A 1000 ml three necked round bottom flask, equipped with condenser, was charged with 1.34 g (0.01M) tetramethyldisiloxane, 296.6 g (1M) Octamethylcyclotetrasiloxane and 6 g acidic ion exchange resin. The solution was stirrer for 12 h at 55-60° C. to give hydride terminated siloxane.

A 1000 ml three necked round bottom flask, equipped with condenser, was charged with 5.1 g (0.016 M) above compound (A), 237.8 g (0.008M) of compound (B) and 0.0003 g Platinum Karstedt's catalyst and the solution was stirred for 8 h at 90° C. Subsequent deprotection and neutralization with Sodium bicarbonate gave Sodium carboxylate functional polydimethylsiloxane. The polymer had a viscosity of 18 Pas at the shear rate of 10 rad/s when measure by HAAKE Rheometer at 20° C.

Example 9

Preparation of Sodium Carboxylate-Functional Polydimethylsiloxane.

A 1000 ml three necked round bottom flask, equipped with condenser, was charged with 184.28 g (1M) Undecenoic acid and 300 ml toluene. The solution was heated to 70° C. and added 80.7 g (0.5M) Hexamethyldisilazane over the period of 2 h. The solution was stirrer at 70-80° C. for 4 h. The solution was stripped off the solvent and low boiling reagent and the reaction mass was distilled under vacuum at 1-5 Hg pressure and 150-160° C. to give Undecenoic acid trimethylsilylester (A).

A 1000 ml three necked round bottom flask, equipped with condenser, was charged with 6.7 g (0.05M) tetramethyldisiloxane, 370.7 g (1.25M) Octamethylcyclotetrasiloxane and 10 g acidic ion exchange resin. The solution was stirrer for 12 h at 55-60° C. to give hydride terminated siloxane.

A 1000 ml three necked round bottom flask, equipped with condenser, was charged with 11.3 g (0.044 M) above compound (A), 150.7 g (0.02 M) of compound (B) and 0.0001 g Platinum Karstedt's catalyst and the solution was stirred for 8 h at 90° C. Subsequent deprotection and neutralization with Sodium bicarbonate gave Sodium carboxylate functional polydimethylsiloxane. The polymer had a viscosity of 689 Pas at the shear rate of 10 rad/s when measure by HAAKE Rheometer at 20° C.

Example 10

Preparation of Sodium Carboxylate-Functional Polydimethylsiloxane.

A 1000 ml three necked round bottom flask, equipped with condenser, was charged with 184.28 g (1M) Undecenoic acid and 300 ml toluene. The solution was heated to 70° C. and added 80.7 g (0.5M) Hexamethyldisilazane over the period of 2 h. The solution was stirrer at 70-80° C. for 4 h. The solution was stripped off the solvent and low boiling reagent and the reaction mass was distilled under 1-5 mm Hg vacuum and 150-160° C. to give Undecenoic acid trimethylsilylester (A).

A 1000 ml three necked round bottom flask, equipped with condenser, was charged with 6.7 g (0.05M) tetramethyldisiloxane, 185.4 g (0.625M) Octamethylcyclotetrasiloxane and 5 g acidic ion exchange resin. The solution was stirrer for 12 h at 55-60° C. to give hydride terminated siloxane.

A 1000 ml three necked round bottom flask, equipped with condenser, was charged with 10.3 g (0.04 M) above compound (A), 76.4 g (0.02 M) of compound (B) and 0.0001 g Platinum Karstedt's catalyst and the solution was stirred for 8 h at 90° C. Subsequent deprotection and neutralization with Sodium bicarbonate gave Sodium carboxylate functional polydimethylsiloxane. The polymer had a viscosity of 283 Pas at the shear rate of 10 rad/s when measured by HAAKE Rheometer at 20° C.

Example 11

Preparation of Sodium Phosphate-Functional Polydimethylsiloxane.

A 1000 ml three necked round bottom flask, equipped with condenser, was charged with 256.3 g (2 M) allylglycidylether and 0.0003 g platinum Karstedt's catalyst and the solution was heated to 70° C. To the above solution, 134.3 g (1M) tetramethyldisiloxane was added drop wise over the period of 6 h at 70-75° C. and further stirred for 6 h at 90° C. to give epoxy functional tetramethyldisiloxane.

A 1000 ml three necked round bottom flask, equipped with condenser, was charged with 3.9 g (0.03M) above product, 296.6 g (1M) Octamethyldisiloxane and 6 g acidic ion exchange resin and the solution was stirred for 16 h at 70° C. to give epoxy functional polydimethylsiloxane.

A 1000 ml three necked round bottom flask, equipped with condenser, was charged with 150 g (0.005M) above product and 1.2 g (0.01M) Phosphoric acid (85%) and the solution was stirred at 85-90° C. for 4 h. The solution was then cooled to around 15° C. and added 0.8 g (0.02M) sodium hydroxide solution dissolved in 1 ml water and the solution was stirred at 15-20° C. for 2 h to give sodium phosphate functional polydimethylsiloxane. The NMR analysis of the product indicated that the polymer was a phosphate functionalized polyorganosiloxane.

Example 12

Preparation of Sodium Phosphate-Functional Polydimethylsiloxane.

A 1000 ml three necked round bottom flask, equipped with condenser, was charged with 256.3 g (2 M) allylglycidylether and 0.0003 g platinum Karstedt's catalyst and the solution was heated to 70° C. To the above solution, 134.3 g (1M) tetramethyldisiloxane was added drop wise over the period of 6 h at 70-75° C. and further stirred for 6 h at 90° C. to give epoxy functional tetramethyldisiloxane.

A 1000 ml three necked round bottom flask, equipped with condenser, was charged with 11.7 g (0.03M) above product, 222.5 g (0.75M) Octamethyldisiloxane and 5 g acidic ion exchange resin and the solution was stirred for 16 h at 70° C. to give epoxy functional polydimethylsiloxane.

A 1000 ml three necked round bottom flask, equipped with condenser, was charged with 152.7 g (0.03M) above product and 7.0 g (0.06M) Phosphoric acid (85%) and the solution was stirred at 85-90° C. for 4 h. The solution was then cooled to around 15° C. and added 4.8 g (0.12M) sodium hydroxide solution dissolved in 5 ml water and stirred the solution at 15-20° C. for 2 h to give sodium phosphate functional polydimethylsiloxane. The NMR analysis of the product indicated that the polymer was a phosphate functionalized polyorganosiloxane.

Lip color formulations (CF 1-11) prepared with the end-functionalized ionic silicones of Examples 3-12, supra, but without a film-forming agent (Comparison Formulations) are set forth in Table 1 as follows:

TABLE 1

Comparison Lip Color Formulations (CF1-11)

| Components, Amount (g) | CF1 | CF2 | CF3 | CF4 | CF5 | CF6 | CF7 | CF8 | CF9 | CF10 | CF11 |
|---|---|---|---|---|---|---|---|---|---|---|---|
| Ionic Silicone of Example 3 | 2.5 | — | — | — | — | — | — | — | — | — | — |
| Ionic Silicone of Example 4 | — | 2.5 | — | — | — | — | — | — | — | — | — |
| Ionic Silicone of Example 5 | — | — | 2.5 | — | — | — | — | — | — | — | — |
| Ionic Silicone of Example 6 | — | — | — | 2.5 | — | — | — | — | — | — | — |
| Ionic Silicone of Example 7 | — | — | — | — | 2.5 | — | — | — | — | — | — |
| Ionic Silicone of Example 8 | — | — | — | — | — | 2.5 | — | — | — | — | — |
| Ionic Silicone of Example 9 | — | — | — | — | — | — | 2.5 | — | — | — | — |
| Ionic Silicone of Example 10 | — | — | — | — | — | — | — | 2.5 | — | — | — |
| Ionic Silicone of Example 11 | — | — | — | — | — | — | — | — | 2.5 | — | — |
| Ionic Silicone of Example 12 | — | — | — | — | — | — | — | — | — | 2.5 | — |
| SE30 (Silicone Gum), Momentive Performance Materials | — | — | — | — | — | — | — | — | — | — | 1.0 |
| SR1000 (Silicone Resin), Momentive Performance Materials | — | — | — | — | — | — | — | — | — | — | 1.5 |
| Bentone Gel VS-5 PC V (Thickener), Elementis Specialties Inc. | 0.81 | 0.81 | 0.81 | 0.81 | 0.81 | 0.81 | 0.81 | 0.81 | 0.81 | 0.81 | 0.81 |
| D5 (Solvent), Momentive Performance Materials | 4 | 4 | 4 | 4 | 4 | 4 | 4 | 4 | 4 | 4 | 4 |
| Red Shade Dispersion "GE" (Pigment), International Foodcraft Corp. | 2.4 | 2.4 | 2.4 | 2.4 | 2.4 | 2.4 | 2.4 | 2.4 | 2.4 | 2.4 | 2.4 |
| TiO2— MT100 TV (Pigment), Tri-K Industries | 0.29 | 0.29 | 0.29 | 0.29 | 0.29 | 0.29 | 0.29 | 0.29 | 0.29 | 0.29 | 0.29 |
| DI Water | — | — | — | — | — | 1.24 | 1.24 | 1.24 | 1.24 | 1.24 | — |
| Glycerin (Moisturizer), Sigma-Aldrich Inc. | 1.24 | 1.24 | 1.24 | 1.24 | 1.24 | — | — | — | — | — | — |

Lip color formulations (F1-F30) prepared with a mixture of end-functionalized ionic silicone (I) and film-forming agent in accordance with the invention are set forth in Tables 2 to 5 as follows:

TABLE 2

Lip Color Formulations Containing Mixtures of Sulfonated Ionic Silicone and Film-forming Agent

| Components, Amount (g) | F1 | F2 | F3 | F4 | F5 | F6 | F7 | F8 | F9 |
|---|---|---|---|---|---|---|---|---|---|
| Ionic Silicone of Example 3 | 1.0 | 1.0 | 1.0 | 1.0 | 1.0 | 2.0 | 1.0 | — | — |
| Ionic Silicone of Example 4 | — | — | — | — | — | — | — | 1.0 | — |
| Ionic Silicone of Example 5 | — | — | — | — | — | — | — | — | 1.0 |
| SR1000 (Silicone Resin), Momentive Performance Materials | 1.5 | — | — | — | — | — | — | 1.5 | 1.5 |
| SilForm (Flexible Resin), Momentive performance Materials | — | 1.5 | — | — | — | — | — | — | — |
| Cloisite 30B (Nanoclay), Southern Clay Products | — | — | 1.5 | — | — | — | — | — | — |
| Montmorillolite K10 (Clay), Sigma-Aldrich Inc. | — | — | — | 1.5 | — | — | — | — | — |
| Ganex ® V-220 (VP/Eicosene Copolymer), ISP Corp. | — | — | — | — | 1.5 | — | — | — | — |
| Covacryl E14 (Acrylate Copolymer), Sensient Cosmetic Technologies | — | — | — | — | — | 1.5 | — | — | — |
| Koboguard 5400 (polycyclopentadiene), Kobo Products Inc. | — | — | — | — | — | — | 2.15 | — | — |
| Bentone Gel VS-5 PC V (Thickener), Elementis Specialties Inc. | 0.61 | 0.81 | 0.81 | 0.81 | 0.81 | 0.81 | 0.81 | 0.81 | 0.81 |
| D5 (Solvent), Momentive Performance Materials | 4 | 4 | 4 | 4 | 4 | 4 | 3.3 | 4 | 4 |
| Red Shade Dispersion "GE" (Pigment), International Foodcraft Corp. | 2.4 | 2.4 | 2.4 | 2.4 | 2.4 | 2.4 | 2.4 | 2.4 | 2.4 |
| TiO2— MT100 TV (Pigment), Tri-K Industries | 0.29 | 0.29 | 0.29 | 0.29 | 0.29 | 0.29 | 0.29 | 0.29 | 0.29 |
| Glycerin (Moisturizer), Sigma-Aldrich Inc. | 1.24 | 1.24 | 1.24 | 1.24 | 1.24 | — | 1.24 | 1.24 | 1.24 |

TABLE 3

Lip Color Formulations Containing Mixtures of Pendant Sulfonated Ionic Silicone and Film-forming Agent

| Components, Amount (g) | F10 | F11 | F12 | F13 | F14 | F15 | F16 | F17 |
|---|---|---|---|---|---|---|---|---|
| Ionic Silicone of Example 6 | 1.0 | 2.0 | 1.0 | 1.0 | 1.0 | 2.0 | 1.0 | — |
| Ionic Silicone of Example 7 | — | — | — | — | — | — | — | 1.0 |
| SR1000 (Silicone Resin), Momentive Performance Materials | 1.5 | — | — | — | — | — | — | 1.5 |
| Aerosil 300 (Silica), Evonik Industries | — | 0.5 | — | — | — | — | — | — |
| Cloisite 30B (Nanoclay), Southern Clay Products | — | — | 1.5 | — | — | — | — | — |
| Montmorillolite K10 (Clay), Sigma-Aldrich Inc. | — | — | — | 1.5 | — | — | — | — |
| Ganex ® V-220 (VP/Eicosene Copolymer), ISP Corp. | — | — | — | — | 1.5 | — | — | — |
| Covacryl E14 (Acrylate Copolymer), Sensient Cosmetic Technologies | — | — | — | — | — | 1.5 | — | — |
| Koboguard 5400 (polycyclopentadiene), Kobo Products Inc. | — | — | — | — | — | — | 2.15 | — |
| Bentone Gel VS-5 PC V (Thickener), Elementis Specialties Inc. | 0.81 | 0.81 | 0.81 | 0.81 | 0.81 | 0.81 | 0.81 | 0.81 |
| D5 (Solvent), Momentive Performance Materials | 4 | 4 | 4 | 4 | 4 | 4 | 3.3 | 4 |
| Red Shade Dispersion "GE" (Pigment), International Foodcraft Corp. | 2.4 | 2.4 | 2.4 | 2.4 | 2.4 | 2.4 | 2.4 | 2.4 |
| TiO2— MT100 TV (Pigment), Tri-K Industries | 0.29 | 0.29 | 0.29 | 0.29 | 0.29 | 0.29 | 0.29 | 0.29 |
| Glycerin (Moisturizer), Sigma-Aldrich Inc. | 1.24 | 1.24 | 1.24 | 1.24 | 1.24 | — | 1.24 | 1.24 |

TABLE 4

Lip Color Formulations Containing Mixtures of Carboxylate-functionalized Ionic Silicone and Film-forming Agent

| Components, Amount (g) | F18 | F19 | F20 | F21 | F22 | F23 | F24 | F25 | F26 |
|---|---|---|---|---|---|---|---|---|---|
| Ionic Silicone of Example 8 | 1.0 | 2.0 | 1.0 | 1.0 | 1.0 | — | — | — | — |
| Ionic Silicone of Example 9 | — | — | — | — | — | 1.0 | 1.0 | 1.0 | — |
| Ionic Silicone of Example 10 | — | — | — | — | — | — | — | — | 1.0 |
| SR1000 (Silicone Resin), Momentive Performance Materials | 1.5 | — | — | — | — | 1.5 | — | — | 1.5 |
| Aerosil 300 (Silica), Evonik Industries | — | 0.5 | — | — | — | — | — | — | — |
| Cloisite 30B (Nanoclay), Southern Clay Products | — | — | 1.5 | — | — | — | 1.5 | — | — |
| Montmorillolite K10 (Clay), Sigma-Aldrich Inc. | — | — | — | 1.5 | — | — | — | 1.5 | — |
| Koboguard 5400 (polycyclopentadiene), Kobo Products Inc. | — | — | — | — | 2.15 | — | — | — | — |
| Bentone Gel VS-5 PC V (Thickener), Elementis Specialties Inc. | 0.81 | 0.81 | 0.81 | 0.81 | 0.81 | 0.81 | 0.81 | 0.81 | 0.81 |
| D5 (Solvent), Momentive Performance Materials | 4 | 4 | 4 | 4 | 3.3 | 4 | 4 | 4 | 4 |
| Red Shade Dispersion "GE" (Pigment), International Foodcraft Corp. | 2.4 | 2.4 | 2.4 | 2.4 | 2.4 | 2.4 | 2.4 | 2.4 | 2.4 |
| TiO2— MT100 TV (Pigment), Tri-K Industries | 0.29 | 0.29 | 0.28 | 0.29 | 0.29 | 0.29 | 0.29 | 0.29 | 0.29 |
| DI Water | 1.24 | 1.24 | 1.24 | 1.24 | 1.24 | 1.24 | 1.24 | 1.24 | 1.24 |

TABLE 5

Lip Color Formulations Containing Mixtures of Phosphate-functionalized Ionic Silicone and Film-forming Agent

| Components, Amount (g) | F27 | F28 | F29 | F30 |
|---|---|---|---|---|
| Ionic Silicone of Example 11 | 1.0 | 2.0 | 1.0 | — |
| Ionic Silicone of Example 12 | — | — | — | 1.0 |
| SR1000 (Silicone Resin) Momentive Performance Materials | 1.5 | — | — | 1.5 |
| Aerosil 300 (Silica) Evonik Industries | — | 0.5 | — | — |
| Cloisite 30B (Nanoclay) Southern Clay Products | — | — | 1.5 | — |
| Bentone Gel VS-5 PC V (Thickener) Elementis Specialties Inc. | 0.81 | 0.81 | 0.81 | 0.81 |
| D5 (Solvent) Momentive Performance Materials | 4 | 4 | 4 | 4 |
| Red Shade Dispersion "GE" (Pigment) International Foodcraft Corp. | 2.4 | 2.4 | 2.4 | 2.4 |
| TiO2-MT100 TV (Pigment) Tri-K Industries | 0.29 | 0.29 | 0.29 | 0.29 |
| DI Water | 1.24 | 1.24 | 1.24 | 1.24 |

A. Transfer Resistance Properties

Transfer resistance measurements were carried out using the method described in U.S. Pat. No. 6,074,654 with the following exceptions:

A uniform coating (thickness-30 micron) of each formulation was made onto an artificial skin film (pre-hydrated over 30% aqueous glycerin solution for 24 h) using an automatic film applicator and dried at 40° C. The films were then subjected a rubbing insult using a tester device. A 500 g mass was covered with a piece of white cotton knit cloth. The assembly was place on the surface of the coated in vitro skin. The assembly was rotated 360°. The cloth was then electronically imaged and the percent area darkened by the red lip formulation transferred was determined by image processing software. The higher the % transfer the more lip formulation transferred from the coated in vitro skin to the white cloth. This process was repeated on the same location of in vitro skin. Each rotation (360°) of the abrasive surface across the dried film was counted as one "insult". The highest limit of transfer coverage is considered to be 100%, which means the entire abrasive surface is covered by colored material. Lower % transfer is indicative of better transfer resistance.

The results of the transfer testing are set forth in Tables 6-10 as follows:

TABLE 6

Transfer Results-Comparison Formulations (CF1-11)

|  | CF1 | CF2 | CF3 | CF4 | CF5 | CF6 | CF7 | CF8 | CF9 | CF10 | CF11 |
|---|---|---|---|---|---|---|---|---|---|---|---|
| Insult 1 | 59% | 55% | 36% | 67% | 61% | 56% | 37% | 30% | 67% | 37% | 22% |
| Insult 2 | 23% | 19% | 13% | 24% | 19% | 17% | 11% | 4% | 18% | 11% | 19% |
| Insult 3 | 13% | 78% | 7% | 7% | 5% | 7% | 4% | 3% | 8% | 4% | 14% |
| Insult 4 | 4% | 4% | 2% | 3% | 2% | 9% | 4% | 2% | 3% | 4% | 10% |
| Insult 5 | 3% | 3% | 2% | 3% | 1% | 3% | 1% | 0% | 3% | 1% | 5% |

TABLE 7

Transfer Results-End-capped Ionic Silicones and Film-forming Agents (F1-9)

|  | F1 | F2 | F3 | F4 | F5 | F6 | F7 | F8 | F9 |
|---|---|---|---|---|---|---|---|---|---|
| Insult 1 | 4% | 46% | 18% | 32% | 13% | 30% | 24% | 26% | 9% |
| Insult 2 | 4% | 22% | 20% | 18% | 27% | 11% | 16% | 22% | 7% |
| Insult 3 | 6% | 11% | 15% | 10% | 18% | 6% | 8% | 20% | 9% |
| Insult 4 | 4% | 5% | 7% | 7% | 7% | 3% | 6% | 7% | 3% |
| Insult 5 | 4% | 1% | 3% | 4% | 3% | 2% | 3% | 5% | 1% |

TABLE 8

Transfer Results-Pendant Sulfonated Silicones and Film-forming Agents (F10-F17)

|  | F10 | F11 | F12 | F13 | F14 | F15 | F16 | F17 |
|---|---|---|---|---|---|---|---|---|
| Insult 1 | 48% | 29% | 40% | 58% | 32% | 67% | 47% | 16% |
| Insult 2 | 29% | 27% | 25% | 23% | 36% | 14% | 21% | 13% |
| Insult 3 | 9% | 13% | 13% | 6% | 20% | 7% | 6% | 14% |
| Insult 4 | 10% | 7% | 5% | 3% | 7% | 3% | 4% | 4% |
| Insult 5 | 11% | 4% | 3% | 2% | 3% | 4% | 2% | 3% |

TABLE 9

Transfer Results-Caboxylate-functionalized Ionic Silicones and Film-forming Agents (F18-F26)

|  | F18 | F19 | F20 | F21 | F22 | F23 | F24 | F25 | F26 |
|---|---|---|---|---|---|---|---|---|---|
| Insult 1 | 34% | 20% | 6% | 9% | 26% | 0% | 5% | 5% | 0% |
| Insult 2 | 11% | 15% | 10% | 10% | 13% | 0% | 5% | 2% | 0% |
| Insult 3 | 5% | 7% | 15% | 13% | 10% | 0% | 4% | 2% | 1% |
| Insult 4 | 4% | 3% | 5% | 8% | 6% | 0% | 4% | 1% | 0% |
| Insult 5 | 6% | 2% | 3% | 10% | 3% | 0% | 2% | 1% | 0% |

TABLE 10

Transfer Results-Phosphate-functionalized Ionic Silicones and Film-forming Agents (F27-F30)

|  | F27 | F28 | F29 | F30 |
|---|---|---|---|---|
| Insult 1 | 39% | 25% | 37% | 1% |
| Insult 2 | 21% | 17% | 17% | 5% |
| Insult 3 | 9% | 12% | 9% | 9% |
| Insult 4 | 9% | 7% | 7% | 16% |
| Insult 5 | 7% | 5% | 6% | 23% |

B. Tackiness Properties

The in vitro skin was prepared in the same manner as described in transfer resistance measurement mentioned in the above examples. Once the formulation was dried on the in vitro skin, the tack force of the dried films were measure using Dia-Stron (MTT 175) instrument, the lower the tack-force, the lesser the tackiness. The results of the tackiness testing are set forth in Table 11 as follows:

TABLE 11

Tackiness Properties

| Tack Force (gmf) | CF3 | CF11 | F1 | F9 |
|---|---|---|---|---|
| Reading 1 | 46.4 | 49.7 | 3.55 | 4.9 |
| Reading 2 | 33.7 | 51.85 | 4.75 | 4.85 |
| Reading 3 | 31.95 | 52.15 | 5.65 | 4.55 |
| Reading 4 | 30.35 | 52.65 | 6.25 | 4.8 |
| Reading 5 | 29.4 | 54.05 | 6.3 | 4.95 |
| Average | 34.36 ± 6.92 | 52.08 +/− 1.57 | 5.3 ± 1.16 | 4.81 ± 0.15 |

C. Gloss Properties

A film of uniform thickness of each formulation was made on a standard leneta card and dried at 40° C. The 60 degree and 85 degree gloss reading of the dried films were recorded using a BYK glossmeter. The glass testing results are set forth in Table 12 as follows:

TABLE 12

Gloss Properties

|  | CF11 | F1 | F9 | F6 | F10 | F17 | F23 |
|---|---|---|---|---|---|---|---|
| 60 degree | 18.5 | 36.2 | 20.5 | 24.1 | 46.4 | 22.4 | 28.1 |
| 85 degree | 66.3 | 78.4 | 72.1 | 42.3 | 77.1 | 69.0 | 77.8 |

D. Trans Epidermal Water Loss (TEWL) Properties

The trans epidermal water loss (TEWL) properties of the cosmetic compositions of the present invention were determined using the method describe in U.S. Pat. No. 5,679,335 with the following exceptions:

The hydrated in vitro skin was coated with individual formulation, dried at 40° C. for overnight. A set of Pyne cups was charged with 3.00 ml of water and covered the cups with dried in vitro skin coated with individual formulation. The rate of water loss from the skin surface was measured using a Tewameter® TM 300 probe attached to MPA 580 instrument. The results of the TEWL treating are set forth in Table 13 as follows:

|  | None | F1 | F26 | F23 |
|---|---|---|---|---|
| TEWL (g/mh$^2$) | 11.0 | 7.7 | 9.3 | 8.4 |

The transfer resistance results herein indicate that lipcolor formulations with a combination of ionic silicone (I) and film-forming agent have better transfer resistance compared to compositions based on unfunctionalized polyorganosiloxane and other comparative ionic silicones alone. The compositions of the invention also show significant improvement in tackiness reduction, gloss and trans epidermal water base compared to an unfunctionalized silicone-based composition.

Hair treatment compositions (HTCs 1-8) were prepared having the formulations set forth below (Table 14) and evaluated for hair curl compression force (results shown in Table 15 below). Each HTC was diluted in cyclodimethicone D5 to form a 5% solid solution in D5. Individual bleached hair tresses (2 g or 6 g tress) were dipped into each solution for 1 min. Excess liquid was squeezed out and each tress was thoroughly dried to remove D5 using a blow drier with a tress being left in an oven at 45° C. overnight. By this procedure, the same amount of silicone was delivered to each hair tress. Tress measurements were made after equilibration in a 50% humidity chamber. Hair curl compression force was measured using Dia-Stron (MU 175) instrument.

Hair treatment compositions of the invention (HTCs 5-8 of Table 14) showed a significant improvement of hair hold properties with the combination of ionic silicones and silicone resins compared to hair treatment compositions containing ionic silicones alone (HTC 1-4 of Table 14).

Additional hair treatment compositions were prepared (HTCs 9-11) having the formulations set forth in Table 16 below. The blends of resin and end-functionalized ionic silicone were diluted in cyclodimethicone D5 to form a 2% solid solution in D5 (HTCs 9 and 10). Single bleached hair tress (2 g weight or 6 g tress) was dipped into the solution for 1 min. Excess liquid was squeezed out and the tress was thoroughly dried to remove D5 using a blow drier after which the tress was left in an oven at 45° C. overnight. By this procedure, the same amount of silicone was delivered to the hair. Tress measurements were taken after equilibration in a 50% humidity chamber. Hair coefficient of friction µ was measured on a CSM tribometer, on a taut flat tress, with a flat stainless steel probe. Hair was considered smooth when µ<0.12. As shown in Table 16, HTC 9 and 10 exhibited a significant reduction of the hair coefficient of friction (smooth hair) and anti-frizz effect compared to untreated hair of HTC 11 (comparison).

TABLE 3

Hair treatments containing ionic silicones

| Components, Amount (g) | HTC9 | HTC10 | HTC11 (Comparison) |
|---|---|---|---|
| SR1000 (Silicone Resin), Momentive Performance Materials | 1.13 | | |
| SilForm (Flexible Resin), Momentive Performance Materials | | 1.13 | |
| Ionic Silicone of Example 3 | 0.87 | 0.87 | |
| D5 (Solvent), Momentive Performance Materials | 98 | 98 | |
| hair coefficient of friction | 0.11 | 0.106 | 0.16 |
| hair appearance after 90% HR chamber | low frizz | low frizz | very frizzy |

When formulated in a hair care product, the blend of end-functionalized ionic silicone and nonfunctionalized silicone resin can be diluted with a volatile solvent such as a volatile silicone, e.g., ethyl trisiloxane, octyl trisiloxane, cyclodimethicone, etc., or a volatile organic solvent (isododecane). The diluted blend can then be applied to hair in the

TABLE 14

Treatments Compositions Containing Ionic Silicones

| Components, Amount (g) | HTC1 | HTC2 | HTC3 | HTC4 | HTC5 | HTC6 | HTC7 | HTC8 |
|---|---|---|---|---|---|---|---|---|
| Ionic Silicone of Example 3 | 1.25 | | | | 0.5 | | | |
| Ionic Silicone of Example 8 | | 1.25 | | | | 0.5 | | |
| Ionic Silicone of Example 11 | | | 1.25 | | | | | |
| Ionic Silicone of Example 9 | | | | | | | 0.5 | |
| Ionic Silicone of Example 12 | | | | 1.25 | | | | 0.5 |
| SR1000 (Silicone Resin), Momentive Performance Materials | | | | | 0.75 | 0.75 | 0.75 | 0.75 |
| D5 (Solvent), Momentive Performance Materials | 25 | 25 | 25 | 25 | 25 | 25 | 25 | 25 |
| deionized water | 0.5 | 0.5 | 0.5 | 0.5 | 0.5 | 0.5 | 0.5 | 0.5 |

TABLE 15

Multicycles Curl Compression Results

| Composition | HTC1 | HTC2 | HTC3 | HTC4 | HTC5 | HTC6 | HTC7 | HTC8 |
|---|---|---|---|---|---|---|---|---|
| Average peak stiffness (gmf) | 4.4 | 7.8 | 4.3 | 9.5 | 4.9 | 12.1 | 11.8 | 11.5 | form of an aqueous or non-aqueous spray, an aqueous or non-aqueous foam, a W/O emulsion or an O/W emulsion.

These and other hair treatment formulations known and conventional can contain other ingredients used in hair care products such as humectants (e.g., panthenol, butylene glycol, sorbitol, glycerin, other polyols, etc.), amino acids and natural moisturizing agents (e.g., the sodium salt of pyrrolidone carbonic acid), nonionic waxes (e.g., fatty alcohols, ethoxylated waxes, glycerol stearate, bee waxes, paraffin waxes, etc.), cationic surfactants, esters, triglyceride oils (e.g., olive oil, jojoba oil, sunflower oil, coconut oil, argan oil, grapeseed oil, etc.), natural butters (e.g., shea butter, cocoa butter), emulsifiers (e.g., silicone emulsifiers, silicone polyether copolymers, organic emulsifiers, etc.), anionic and amphoteric surfactants (e.g., ecocobetaine, SLES, isothionate, sugar surfactants, etc.), spreading agents (e.g., silicone superspreaders, etc.), solid particulates (e.g., pigments, minerals, talc, micas, iron oxides, boron nitride, titanium oxide, clays, etc.), permanent and semi-permanent hair dyes, fragrances, actives such as plant extracts, polyphenols, polysaccharides (e.g., chitosan), proteins (e.g., keratin, silk protein, wheat proteins, etc.), lipids, sterols and antidandruff actives (e.g., zinc pyrithione, selenium sulfide, antifungal agents, etc.), salicylic acid, glycolic acid, hair growth actives, anti-aging actives (e.g., retinol, alpha-hydroxy acids, etc.), niacinamide, reducing agents (e.g., thioglycolates, cysteamine, etc.), sulfites, oxidizing agents (e.g., hydrogen peroxide, bromates, etc.), relaxers (e.g., sodium hydroxides, guanidines, etc.), crosslinking agents (e.g., aldehydes, epoxy containing compounds, silanes, enzymes, etc.), styling polymers (e.g., PVP, acrylate copolymers, etc.), thickening polymers (e.g., acrylates, polyacrylamide, cellulose, starch, polysaccharide gums, pectins, etc.), deposition aid polymers (e.g., cationic guars, cationic cellulose, merquats, etc.), preservatives, biocides (e.g., phenoxyethanol, potassium sorbate, benzoic acid, sorbic acids, etc.), fragrances, antioxidants (e.g., vitamin E), UVA and UVB sunscreens, sunless tanning agents (e.g., dihydroxyacetone, and the like).

Combing oils (COs) for treating kinky hair were prepared as shown in Table 17. Each CO was spread on undamaged kinky hair (Hair International Inc.) to obtain a dose on hair of 0.25 g/g. The hair was combed through with a fine tooth comb and the total distance of comb travel was measured with a ruler. CO effectiveness is exhibited where comb travel distance is greater than that for untreated hair.

As shown in Table 17, untreated hair (CO3, Comparison) showed a poor combability. Comparative 1 was the hair treated with petrolatum, showing some improvement of combability but a greasy feel. The hair tress treated with CO1 exhibited improved combability and a perceptibly less greasy feel.

TABLE 17

Combing Oils for Kinky hair

| Components, Amount (g) | CO1 | CO2 | CO3 (Comparison) |
|---|---|---|---|
| petrolatum snow white | 49 | 100 | |
| Ionic Silicone of Example 5 | 49 | | |
| deionized water | 2 | | |
| disentangling length (cm) | 5 | 4 | 3 |
| Feel | smooth | greasy | clean |

Water-in-oil emulsions (WOs 1-6) containing various ionic silicones in accordance with the invention were prepared as shown below in Table 18.

TABLE 18

Water-in-Oil Emulsion Containing Ionic Silicones

| Components, Amount (g) | WO1 | WO2 | WO3 | WO4 | WO5 | WO6 |
|---|---|---|---|---|---|---|
| Silform 60A, Momentive Performance Materials | 2 | 2 | 2 | 2 | 2 | 2 |
| Isododecane (Solvent), Presperse LLC | 10 | 10 | 10 | 10 | 10 | 10 |
| Silsoft ETS, Momentive Performance Materials | 10 | 10 | 10 | 10 | 10 | 10 |
| SR1000 (Silicone Resin), Momentive Performance Materials | 5 | 5 | 5 | 5 | 5 | 5 |
| Ionic Silicone of Example 3 | 2.5 | 0 | 0 | 0 | 0 | 0 |
| Ionic Silicone of Example 5 | 0 | 2.5 | 0 | 0 | 0 | 0 |
| Ionic Silicone of Example 6 | 0 | 0 | 2.5 | 0 | 0 | 0 |
| Ionic Silicone of Example 7 | 0 | 0 | 0 | 2.5 | 0 | 0 |
| Ionic Silicone of Example 8 | 0 | 0 | 0 | 0 | 2.5 | 0 |
| Ionic Silicone of Example 11 | 0 | 0 | 0 | 0 | 0 | 2.5 |
| NaCl | 0.8 | 0.8 | 0.8 | 0.8 | 0.8 | 0.8 |
| butylene glycol | 3 | 3 | 3 | 3 | 3 | 3 |
| deionized water | 66.7 | 66.7 | 66.7 | 66.7 | 66.7 | 66.7 |

Oil-in-water emulsions (OWs 1-7) containing the ionic silicone of Example 5, supra, were prepared as shown below in Table 19.

TABLE 19

Oil-in-Water Emulsion Containing Ionic Silicone

| Components, Amount (g) | OW1 | OW2 | OW3 | OW4 | OW5 | OW6 | OW7 |
|---|---|---|---|---|---|---|---|
| AMP-95 (aminomethyl propanol), Dow Chemical | 0.56 | | | | | | 0.7 |
| Aculyn 160 (Acrylates/Hydroxyesters Acrylates Coppolymer), Dow Chemical | 2 | | | | | | |
| Aculyn 88 (Acrylates/Steareth-20 Methacrylate Crosspolymer), Dow Chemical | 5 | | | | | | |
| Cellosize PCG-10 (hydroxyelthyl cellulose), Dow Chemical | | 1.5 | | | | | |
| Ucare JR-30M (polyquaternium-10), Dow Chemical | | 0.05 | | | | | |
| Ssepigel 305, SEPPIC | | | 5 | | | | |
| Aristoflex AVC, Clariant | | | | 2 | | | |
| Carbopol 980, Lubrizol | | | | | | | 0.8 |
| Fixate G-100, Lubrizol | | | | | | | 2.6 |
| Ultrez 20, Lubrizol | | | | 0.2 | | | |
| Carbopol Aqua SF-1 (30%), Lubrizol | | | | | | 1 | |
| glyceryl stearate and PEG-100 stearate, | | | | | | 2 | 6 |

TABLE 19-continued

Oil-in-Water Emulsion Containing Ionic Silicone

| Components, Amount (g) | OW1 | OW2 | OW3 | OW4 | OW5 | OW6 | OW7 |
|---|---|---|---|---|---|---|---|
| HallStar cetearyl alcohol, Sigma Aldrich | | | | | 1 | 3 | |
| sodium hydroxide (18%) | | | | | 0.2 | 0.2 | |
| Panthenol, Sigma Aldrich | | | | | 0.5 | 0.5 | |
| disodium EDTA | | | | | 0.05 | 0.05 | |
| SR1000 (silicone resin), Momentive Performance Materials | 5 | 5 | 5 | 5 | 5 | 5 | 5 |
| Ionic Silicone of Example 5 | 2.5 | 2.5 | 2.5 | 2.5 | 2.5 | 2.5 | 2.5 |
| D5 (Solvent), Momentive Performance Materials | 7 | 7 | 7 | | | | 7 |
| Isododecane (Solvent), Presperse LLC | | 7 | | | | 7 | |
| silsoft ETS, Momentive Performance Materials | | | 7 | 7 | 7 | | |
| deionized water | q.s 100 | q.s 100 | q.s 100 | q.s 100 | q.s 100 | q.s 100 | q.s 100 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

The invention claimed is:

1. A personal care composition comprising at least one end-functionalized ionic silicone and at least one film-forming agent wherein the silicone comprises at least two terminal ionic groups that form ionic aggregates and where the ionic interactions have a reversible nature, and the film-forming agents is selected from the group consisting of organosiloxane resins, hydrocarbon polymers, hydrocarbon polymer containing at least one heteroatom, fluorine atom-containing hydrocarbon polymers and clays, wherein the end-functionalized ionic silicone is of the formula:

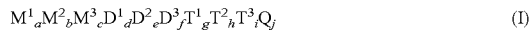   (I)

wherein:
$M^1 = R^1R^2R^3SiO_{1/2}$
$M^2 = R^4R^5R^6SiO_{1/2}$
$M^3 = R^7R^8R^9SiO_{1/2}$
$D^1 = R^{10}R^{11}SiO_{1/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ in which:
$R^1$, $R^2$, $R^3$, $R^5$, $R^6$, $R^8$, $R^9$, $R^{10}$, $R^{11}$, $R^{13}$, $R^{15}$ and $R^{16}$ each independently is an aliphatic, aromatic or fluoro monovalent hydrocarbon group having from 1 to 60 carbon atoms;

$R^4$, $R^{12}$ and $R^{17}$ each independently is a monovalent group bearing ion-pairs and having the formula -A-$I^xM_n^{y+}$, or zwitterion having the formula —R'—N$^+$(R")$_2$—R'"—I$^-$, in which A is a spacing moiety having at least one spacing atom, the spacing moiety being selected from the group consisting of divalent hydrocarbon group and hydrocarbonoxy group, 1 is an ionic group, R' is a divalent hydrocarbon group having from 1 to 20 carbon atoms, R" is a monovalent hydrocarbon group having from 1 to 20 carbon atoms, R'" is a divalent hydrocarbon group having from 2 to 20 carbon atoms, and each M independently is hydrogen or a cation independently selected from alkali metals, alkali earth metals, transition metals, quaternary ammonium groups and phosphonium groups;

$R^7$, $R^{14}$ and $R^{18}$ each independently is —CH$_2$CH(R$^{19}$)(C$_n$H$_{2n}$)—O—(C$_2$CH$_4$O)$_o$—(C$_3$H$_6$O)$_p$—(C$_4$H$_8$O)$_q$—R$^{19}$ in which R$^{19}$ is hydrogen or an R$^1$ group as defined above;

superscripts x and y are positive integers subject to the limitation that x=ny;

each subscript n independently has a value of from 0 to 6 and subscripts o, p and g each independently has a value of from 0 to 1000, subject to the limitation that o+p+q≥1; and, subscripts a, c, d, e, f, g, h, i and j each independently is zero or a positive integer subject to the limitations that 2≤a+b+c+d+e+f+g+h+i+j≤4500 and b>2.

2. The personal care composition of claim 1 wherein in end-functionalized ionic silicone (I), each $R^1$, $R^2$, $R^3$, $R^5$, $R^6$, $R^8$, $R^9$, $R^{10}$, $R^{11}$, $R^{13}$, $R^{15}$ and $R^{16}$ group is independently selected from methyl, ethyl, n-propyl, iso-propyl, n-butyl, isobutyl, tert-butyl, n-pentyl, iso-pentyl, neopentyl, tert-pentyl, hexyl, heptyl, octyl, nonyl, decyl, cyclopentyl, cyclohexyl, cycloheptyl, methylcyclohexyl, naphthyl; tolyl, xylyl, ethylphenyl and benzyl.

3. The personal care composition of claim 1 wherein in end-functionalized ionic silicone (I), divalent spacing group A is an alkylene group —(CHR$^{20}$)$_m$— wherein R$^{20}$ is hydrogen or an R$^1$ group and subscript m is a positive integer ranging from 1 to 100.

4. The personal care composition of claim 1 wherein in end-functionalized ionic silicone (I), divalent spacing group A is an arylene group selected from —(CHR$^{21}$)$_k$—C$_6$H$_4$(CH$_2$)$_r$— —CH$^2$CH(R')(CH$_2$)$_k$C$_6$H$_4$— or —CH$_2$CH(R$^{22}$)(CH$_2$)$_r$C$_6$H$_3$R$^{23}$ wherein R' is hydrogen or an R$^1$ group, R$^{21}$ is hydrogen or an R$^1$ group, R$^{22}$ is hydrogen or an R$^1$ group, R$^{23}$ is a monovalent radical of from 1 to 20 carbon atoms and subscripts k and r are zero or positive integers subject to the limitation 0≤k+r≤100.

5. The personal care composition of claim 1 wherein in end-functionalized ionic silicone (I), divalent spacing group A is a hydrocarbonoxy group selected from —(CHR$^{24}$)$_s$—(O—CHR$^4$CH$_2$)$_{s'}$, and —O—(CH$_2$)$_t$ wherein R$^{24}$ is hydrogen or an R$^1$ group, s has a value of from 0 to 50, s' has a value of from 1 to 50 and t has a value of from 0 to 50 subject to the limitation 1≤s+s'+t≤100.

6. The personal care composition of claim 1 wherein in end-functionalized ionic silicone (I), I$^-$ in the ion-pairbearing group and in the zwitterion is selected from sulfonate —SO$_3^-$ and sulfate —OSO$_3$.

7. The personal care composition of claim 1 wherein in end-functionalized ionic silicone (I), M$^+$ is selected from Li, Na, K, Cs, Mg, Ca, Ba, Zn, Cu, Fe, Ni, Ga, Al, Mn, Cr, Ag, Au, Pt, Pd, Ru and Rh.

8. The personal care composition of claim 1 wherein in end-functionalized ionic silicone (I), in the zwitterion, R' is a divalent hydrocarbon radical having from 1 to 20 carbon atoms, R" is a monovalent hydrocarbon radical having from 1 to 20 carbon atoms and R'" is a divalent hydrocarbon radical having from 2 to 20 carbon atoms.

9. The personal care composition of claim 1 wherein in end-functionalized ionic silicone (I), subscripts a, c, d, e, f, g, h, i and j each independently is zero or a positive number subject to the limitations that 2≥a+b+c+d+e+f+g+h+i+j≥4500, b>2.

10. The personal care composition of claim 9 wherein in end-functionalized ionic silicone (I), subscript b is 2; subscripts a, c, e, f, g, h, i, j, k, l and m are 0; subscript d is from 5 to 1000, R$^5$, R$^6$, R$^{10}$ and R$^{11}$ are methyl or ethyl; R$^{10}$ is —CH$_2$CH(H or CH$_3$)-A-SO$_3$M; A is a divalent benzyl radical; and, M$^+$ is Li, Na, K, Ag, a quaternary ammonium group, ammonium salt or phosphonium group.

11. The personal care composition of claim 1 wherein end-functionalized ionic silicone (I) is at least one of sodium sulfonate-capped polydimethylsiloxane, silver sulfonate-capped polydimethylsiloxane, magnesium sulfonate-capped polydimethylsiloxane, calcium sulfonate-capped polydimethylsiloxane, zinc sulfonate-capped polydimethylsiloxane and triethanolammonium sulfonate-capped polydimethylsilane.

12. The personal care composition of claim 1 wherein the organosiloxane film-forming agent contains combinations of R$_3$SiO$_{12}$, R$_2$SiO, RSiO$_{3/2}$, and SiO$_2$ units in ratios to each other that satisfy the relationship R$_n$SiO$_{(4-n)/2}$ where n is a value between 0 and 1.50 and R is independently selected from methyl, trifluoromethyl, phenylenemethyl and phenyl groups.

13. The personal care composition of claim 1 wherein the hydrocarbon polymer film-forming agent is at least one member selected from the group consisting of polybutene, polyisobutene, polycyclopentadiene, petroleum jelly and mineral oil.

14. The personal care composition of claim 1 wherein the hydrocarbon polymer containing at least one heteroatom is at least one member selected from the group consisting of polyvinylpyrrolidone (PVP)/eicosene copolymer, PVP/hexadecene copolymer, acrylate copolymer and polyvinyl alcohol.

15. The personal care composition of claim 1 wherein the film-forming clay is at least one member selected from the group consisting of modified clays, unmodified clays, cloisite 30B, momtmorillite (NaMMT), LDH and bentonite.

16. The personal care composition of claim 1 further comprising at least one non-functionalized silicone.

17. The personal care composition of claim 1 further comprising at least one organic solvent.

18. The personal care composition of claim 1 formulated as an oil-in-water or water-in-oil emulsion.

19. The personal care composition of claim 1 wherein said personal care composition is selected from the group consisting of deodorants, antiperspirants, sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations thereof.

20. The personal care composition of claim 1 wherein said personal care composition is selected from the group consisting of deodorants, antiperspirants, sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations thereof.

\* \* \* \* \*